United States Patent [19]

Woo

[11] 4,013,736

[45] Mar. 22, 1977

[54] SYNTHESIS OF LOW VISCOSITY LOW POUR POINT HYDROCARBON LUBRICATING OILS

[75] Inventor: Charles Woo, Sarnia, Canada

[73] Assignee: Exxon Research and Engineering Company, Linden, N.J.

[22] Filed: July 16, 1975

[21] Appl. No.: 596,308

[52] U.S. Cl. .......................... 260/676 R; 260/671 B; 260/680 B; 260/683.15 R

[51] Int. Cl.$^2$ .......................................... C07C 3/20

[58] Field of Search ............... 260/683.15 R, 680 B, 260/671 B, 671 C, 676 R

[56] References Cited

UNITED STATES PATENTS 3,562,148 2/1971 Mitschc .................... 260/683.15 R

*Primary Examiner*—C. Davis

*Attorney, Agent, or Firm*—Byron O. Dimmick; Frank T. Johmann

[57] ABSTRACT

Synthetic hydrocarbon lubricating oils with very low pour points and low viscosities are produced by polymerizing alpha-olefins of from 5 to 20, preferably 10 to 14 carbon atoms, at temperatures in the range of 300° to 800° F in the presence of an acidic catalyst of the crystalline aluminosilicate zeolite molecular sieve-type. The products are predominantly of the paraffinic and naphthenic hydrocarbon types. Aromaticity can be introduced by polymerizing the olefins in the presence of aromatic hydrocarbons such as benzene. The products are useful as lubricants in arctic climates and in other applications where low pour points are required, such as for transformer oils.

5 Claims, No Drawings

SYNTHESIS OF LOW VISCOSITY LOW POUR POINT HYDROCARBON LUBRICATING OILS

BACKGROUND OF THE INVENTION

It is known to polymerize alpha-olefins in the range of from 5 to 20 carbon atoms either thermally or in the presence of catalysts to give products having viscosities in the lubricating oil range. Normally such lubricants have undesirably high pour points, e.g. in the range of about 0° F to +70° F. Such products are not suitable for applications where low pour points and low viscosities are required, as for example, in transformer oils. Lubricating oils having low pour points and low viscosities making them useful as electrical insulating oils for transformers and switches are normally derived either from naphthenic crude oils, which are becoming scarce, or by extensive and costly processing of conventional lubricating oil distillates. The present invention provides a process for preparing very low pour point, low viscosity products by polymerizing alpha-olefins of from 5 to 20, preferably 10 to 14 carbon atoms in the presence of a molecular-sieve-type catalyst.

REFERENCES TO THE PRIOR ART

U.S. Pat. No. 2,620,365 of J. A. Anderson teaches the contacting of alpha-olefins of from 15 to 25 carbon atoms with alumina-type catalysts at 300° to 650° F to cause isomerization of the olefins in preparation for their subsequent polymerization of synthetic lubricating oils by reaction with aluminum chloride. More particularly, in the case of silica-alumina catalysts, contacting temperatures of about 375° to 500° F are employed and only small amounts of polymer are formed in the contacting with silica-alumina catalyst. U.S. Pat. No. 3,843,511 of Charles M, Selwitz teaches the preparation of synthetic petrolatum by contacting alpha-olefins of from 30 to 50 carbon atoms with silica-alumina at temperatures of 200° to 260° C.

DESCRIPTION OF THE PRESENT INVENTION

The present invention provides a process wherein very low pour point, low viscosity stable synthetic hydrocarbon lubricating oils are prepared by polymerizing alpha-olefins of from 5 to 20 carbon atoms in the presence of an acidic catalyst of the type that is known as an alumino-silicate molecular sieve. The products that are obtained are predominantly isoparaffins and substituted one-ring and two-ring naphthenes. Products containing some aromatic rings can be obtained by conducting the polymerization in the presence of benzene or alkylbenzene having a short chain alkyl group. The products of this invention will have viscosities of less than 100, preferably less than 65 SUS at 100° F and pour points no greater than −40° F and preferably no greater than −50° F.

Among the aluminosilicate molecular sieve catalysts that can be employed in the present invention are those described in British Pat. No. 1,000,901 and in U.S. Pat. No. 2,971,903. Encapsulated zeolites can also be used. See, for example, U.S. Pat. Nos. 3,558,476 and 3,649,521.

The olefins that are employed in the process of this invention are alpha-olefins, that is, aliphatic terminal olefins having from about 5 to 20, preferably 10 to 14 carbon atoms, e.g. n-hexane, n-decene, n-dodecene, n-tetradecene and n-octadecene. Sources of such olefins include the cracking of paraffin wax, the polymerization of other olefins such as ethylene, and the dehydration of alcohols. Another very desirable source is the product obtained from the steam cracking of a petroleum hydrocarbon fraction such as a paraffin wax, a petroleum gas oil or a raffinate obtained by the solvent refining of a gas oil fraction. In the steam cracking operation, the hydrocarbon vapors of the hydrocarbon feedstock are mixed with a sufficiently high proportion of steam to form a cracking feed mixture containing about 10 to 500 mol percent, preferably about 60 to 90 mol percent, of steam, the cracking being conducted at a temperature within the range of about 900° to about 1400° F, or more usually between about 1000° and 1200° F, with a residence time of generally between about 0.1 and 30 seconds, more usually between about 0.5 and 5 seconds. The cracking pressure will generally be in the range of about 1 to 3 atmospheres. The resulting steam cracked hydrocarbon fraction is subjected to a fractional distillation in order to obtain a cut containing olefins having in the range of 5 to 20 carbon atoms.

The polymerization reaction used in the process of this invention involves contacting the olefins with the molecular sieve zeolite catalyst at a temperature within the range of about 300° to 800° F, preferably about 500° to 700° F. in the presence of from about 0.5 to 20 weight percent of the catalyst, preferably from about 1 to about 10 weight percent of the catalyst based on the olefin feed. The time of the reaction will depend on reaction conditions and must be sufficient for its completion, which can be readily determined by distillation of a sample to remove unpolymerized materials, Usually the reaction will take place within a period of about 1 to 10 hours. The reaction pressure can be atmospheric as well as above or below atmospheric. Usually, the pressure attained when the reactants are placed in a sealed reactor at ordinary pressure and temperature and then heated to the desired reaction temperature will be satisfactory. One representative set of conditions is 600° F temperature, 600 psig pressure, and one hour residence time. The reaction can be conducted under an inert atmosphere such as one of nitrogen although this is not necessary.

The product of the polymerization is normally separated from the catalyst by filtration and the liquid phase is desirably subjected to a distillation step to remove overhead all fractions that boil up to about 550° F at atmospheric pressure, these being principally unpolymerized olefins which can be recycled to the polymerization stage.

The distillation bottoms as such, or a selected fraction thereof such as the 550°–800° F fraction, are preferably subjected to a conventional hydrofinishing treatment to remove any unsaturation. Conventional hydrofinishing conditions can be used employing conventional catalysts such as nickel, cobalt molybdate and the like.

In a modification of the process, the alpha-olefins can be polymerized in the presence of benzene, or a short chain alkylbenzene, or styrene to give a product having aromatic groups as well as naphthenic groups. The alkyl benzenes will have alkyl groups of from 1 to 4 carbon atoms, and preferably 1 to 2 carbon atoms, and include methylbenzene, ethylbenzene, and propylbenzene. In the modified process, the proportion of benzene, alkylbenzene or styrene to alpha-olefins can range from about 0.25 to about 2 parts, preferably 0.5 to 1.5 parts, of the aromatic per part of the olefins, by weight.

The invention is illustrated by the following examples which include preferred embodiments.

In the examples, the mixed $C_{10}$ to $C_{14}$ alpha-olefin feed that was used was obtained by the steam cracking of paraffin wax under mild conditions. A typical analysis of the mixed $C_{10}$–$C_{14}$ olefins was as follows:

| | |
|---|---|
| Hydrocarbon Component Type, % | |
| Aromatics | 1.1 |
| Saturates | 0.8 |
| Mono-Olefins | 84.9 |
| Polyunsaturated components | 13.2 |
| Carbon Distribution, % | |
| $C_{10}$ | 15.3 |
| $C_{11}$ | 18.5 |
| $C_{12}$ | 20.3 |
| $C_{13}$ | 21.4 |
| $C_{14}$ | 16.0 |
| $C_{15}$ | 8.0 |
| $C_{16}$ | 0.5 |

EXAMPLE 1

The catalyst used in this example consisted of 5 weight percent of a 13 A crystalline aluminosilicate zeolite supported on or encapsulated in 95 weight percent of a silica-alumina matrix having 13 weight percent alumina. See U.S. Pat. No. 3,558,476. The zeolite had been modified by incorporating rare earth metal oxides. The composite catalyst contained 85.2 percent $SiO_2$, 13.4 percent $Al_2O_3$, 1.1 percent rare earth oxides and 0.2 percent of sodium oxide. A mixture of fifteen grams of this catalyst and 300 grams of the mixed $C_{10}$ to $C_{14}$ alpha-olefin feed described above was charged to an autoclave of 1 liter capacity. The temperature was then raised to 650° F over a period of 1 hour and maintained at that level for 2 hours after which the autoclave was cooled. The product that was recovered from the autoclave was filtered to remove the catalyst and the liquid phase distilled to remove overhead all components that boiled up to 550° F. The distillation residue was then subjected to further distillation to recover overhead the fraction that boiled in the range of 550° to 800° F. The 550°–800° F cut represented a 40 weight percent once-through yield on the olefin feed. This cut was then hydrogenated to remove residual unsaturation, the hydrogenation being conducted at 500° F and 800 psi of hydrogen for 1 hour in the presence of 5 weight percent of a nickel catalyst.

Similar polymerization runs were conducted at temperatures ranging from 550° F to 700° F and with catalyst concentrations of either one or five weight percent and with residence times ranging from 1 to 10 hours. For comparison purposes, one run was made at 650° F for 2 hours in the absence of catalyst. The properties of the topped polymer in each run, that is, the residue after removing the fraction that boiled up to 550° F, are given in Table I. The properties of those polymers that were subsequently given a further fractionation to obtain the fraction boiling between 550° F and 800° F and that were then hydrotreated are given in Table II.

TABLE I

| | Properties of Topped Polymer (550° F+) | | | | | | | | | |
|---|---|---|---|---|---|---|---|---|---|---|
| Run | A | B | C | D | E | F | G | H | I | Control |
| % Catalyst | 5 | 5 | 5 | 5 | 5 | 1 | 5 | 5 | 5 | 0 |
| Temp. ° F | 550 | 550 | 600 | 600 | 600 | 650 | 650 | 650 | 700 | 650 |
| Reaction Time, Hrs. | 2 | 10 | 1 | 2 | 10 | 2 | 2 | 10 | 2 | 2 |
| Polymer Inspections | | | | | | | | | | |
| Viscosity SUS/100° F | 69.9 | 73.0 | 64.3 | 65.6 | 82.7 | 60.9 | 68.9 | 87.9 | 66.1 | 195 |
| Viscosity SUS/210° F | 36.7 | 36.6 | 35.6 | 35.7 | 37.5 | 35.2 | 36.1 | 37.6 | 35.7 | 51.0 |
| Viscosity Index | 117 | 94 | 95 | 95 | 86 | 104 | 90 | 77 | 89 | 163 |
| Pour Point, ° F | −50 | −80 | −80 | −80 | −70 | −70 | −80 | −70 | −80 | +35 |
| Yield, Wt% on Olefins | 15 | 57 | 46 | 53 | 53 | 25 | 53 | 46 | 46 | 70 |

TABLE II

| Hydrotreated 550°–800° F Fraction of Polymer Product | | | | |
|---|---|---|---|---|
| Run | D | G | H | Control |
| % Catalyst | 5 | 5 | 5 | 0 |
| Reaction Time, Hrs. | 2 | 2 | 10 | 2 |
| Temp. ° F | 600 | 650 | 650 | 650 |
| Product Inspections | | | | |
| Viscosity, SUS/100° F | 50.5 | 55.2 | 62.4 | 52.7 |
| Viscosity, SUS/210° F | 33.3 | 34.0 | 34.9 | 34.4 |
| Viscosity Index | 92 | 81 | 68 | 143 |
| Pour Point, ° F | −80 | −65 | −70 | +70 |
| Gravity, ° API | 40.3 | 40.5 | 36.8 | — |
| Yield, wt% on Olefin | 39 | 40 | 36 | 19 |

It will be seen from Table I that although there was a greater yield of polymer, based on olefin feed, when no catalyst was used, the product had a pour point of +35° F whereas in each instance where the catalyst was used the pour point was at least as low as −50° F. Referring now to Table II, it will be seen that when the 550°–800° F cut was hydrofinished, the yield of product was only 19 weight percent based on olefin feed when no catalyst was used and the pour point was +70° F. In contrast to this, in those instances where the 550°–800° F fraction of the catalytic reaction was hydrotreated, the products had pour points of −65° to −80° F and the yield based on olefin feed ranged from 36 to 40 weight percent. Moreover, all of the products of the invention met the CSA standard $C_{50}$ for electrical insulating oils for transformers and switches, this standard requiring a pour point no greater than −50° F and a maximum viscosity of 62 SUS at 100° F.

EXAMPLE 2

The molecular sieve catalyst employed in Example 1 was also used in this example. Various mixtures of benzene and the $C_{10}$–$C_{14}$ olefin mixture described above were contacted with the catalyst at temperatures ranging from 550° F to 650° F and at reaction times of from 1 to 10 hours. For example, in one run, the temperature was raised to 600° F in one hour, maintained at that temperature for one hour and then cooled. The products in each run were handled in the same manner as in Example 1. The inspections of the crude polymer in each case and the inspections of the hydrotreated products are given in Table III which follows.

TABLE III

| POLYMERIZATION OF OLEFIN/BENZENE FEEDS | | | | | |
|---|---|---|---|---|---|
| Reaction Conditions | | | | | |
| Run No. | 1 | 2 | 3 | 4 | Control |
| $C_{10}$–$C_{14}$ α-olefins, g | 180 | 100 | 100 | 100 | 100 |
| Benzene, g | 70 | 100 | 100 | 100 | 100 |
| Catalyst, g | 12.5 | 10 | 20 | 40 | none |
| Temperature, ° F | 550 | 600 | 600 | 600 | 650 |
| Time, Hrs. | 10 | 1 | 1 | 1 | 1 |
| Inspections of 550° F + Product | | | | | |
| Yield, wt % on olefins | 69 | 62 | 78 | 82 | 10 |
| Viscosity, SUS/100° F | 63.4 | 53.4 | 57.9 | 58.8 | 98.9 |
| SUS/210° F | 35.3 | 33.7 | 34.3 | 34.4 | 41.5 |
| Viscosity Index | 87 | 83 | 73 | 72 | 162 |
| Pour Point, ° F | −80 | −80 | −80 | −80 | +25 |
| Gravity, ° API | 35.3 | 34.1 | 32.3 | 31.5 | — |
| Hydrotreated 550° F + Product | | | | | |
| Viscosity, SUS/100° F | 70.7 | 60.0 | 63.4 | 66.2 | |
| SUS/210° F | 36.2 | 34.8 | 35.2 | 35.5 | |
| Viscosity Index | 85 | 83 | 77 | 78 | |
| Pour Point, ° F | −80 | −80 | −80 | −80 | |
| Gravity, ° API | 37.2 | 37.1 | 35.4 | 34.8 | |
| Refractive Index at 20° C | 1.4645 | 1.4639 | 1.4694 | 1.4706 | |
| Carbon Type, % Paraffin | 68 | 70 | 66 | 67 | |
| Naphthene | 26 | 26 | 26 | 27 | |
| Aromatic | 6 | 4 | 8 | 6 | |

It will be noted that all of the polymers prepared in the presence of the catalyst had aromatic carbon contents of from 4 to 8%, naphthenic carbon contents of from 26 to 27 weight percent and paraffinic carbon contents of from 66 to 70 percent. In the absence of the catalyst, a very low yield of high V.I., high pour point oil was obtained. In the presence of the catalyst, the yield was substantially increased, the viscosity was lower, and the pour points were very low, thus meeting the objectives of this invention. Comparison with the runs using only the alpha olefins will show that the presence of benzene improved the yield, decreased the viscosity and lowered the pour point.

What is claimed is:

1. A process for the preparation of a synthetic hydrocarbon lubricating oil having a viscosity of less than 100 SUS at 100° F. and a pour point of −40° F. or less, which comprises the polymerization of aliphatic alpha-olefins of from about 5 to 20 carbon atoms at a polymerization temperature in the range of from about 300° to 800° F. for from about 1 to 20 hours in the presence of from about 0.5 to 20 weight percent of a silica-alumina molecular sieve acidic catalyst, fractionating to obtain a fraction boiling within the range of about 550° to 800° F., and then hydrofining said fraction to thereby form said lubricating oil.

2. The process defined by claim 1 wherein the alpha olefins are a mixture of olefins of from about 10 to 14 carbon atoms.

3. The process defined by claim 2, wherein the polymerization temperature is within the range of about 500° to 700° F.

4. The process defined by claim 3, wherein said oil has a pour point no greater than −50° F. and is suitable as an electrical insulating oil, and said catalyst consists of a rare-earth-promoted crystalline alumino-silicate zeolite in a silica-alumina matrix.

5. The process defined by claim 2, wherein the olefins are polymerized in the presence of from about 0.25 to 2 parts by weight of benzene, styrene or an alkylbenzene per part by weight of said alpha-olefin feed, said alkylbenzene having an alkyl group of from 1 to 4 carbon atoms.

* * * * *